United States Patent
Lobato et al.

(10) Patent No.: US 7,842,821 B2
(45) Date of Patent: Nov. 30, 2010

(54) METHOD OF OBTAINING DERIVATIVES OF 4-(N-ALKYLAMINO)-5,6-DIHYDRO-4H-THIENO-[2,3-B]-THIOPYRAN

(75) Inventors: José María Gorgojo Lobato, Boecillo-Valladolid (ES); Luis Octavio Silva Guisasola, Boecillo-Valladolid (ES); Jorge Martín Juárez, Boecillo-Valladolid (ES)

(73) Assignee: Ragactives, S.L., Boecillo-Valladolid (ES)

(*) Notice: Subject to any disclaimer, the term of this patent is extended or adjusted under 35 U.S.C. 154(b) by 624 days.

(21) Appl. No.: 11/718,603

(22) PCT Filed: Nov. 4, 2005

(86) PCT No.: PCT/ES2005/000594

§ 371 (c)(1),
(2), (4) Date: Jun. 22, 2007

(87) PCT Pub. No.: WO2006/051137

PCT Pub. Date: May 18, 2006

(65) Prior Publication Data

US 2009/0076287 A1 Mar. 19, 2009

(30) Foreign Application Priority Data

Nov. 5, 2004 (ES) ................. 200402668

(51) Int. Cl.
*C07D 495/06* (2006.01)
(52) U.S. Cl. ........................................ 549/23
(58) Field of Classification Search ........... 549/23
See application file for complete search history.

(56) References Cited

FOREIGN PATENT DOCUMENTS

EP 0 617 037 A1 3/1994
EP 1 329 453 A1 7/2003

OTHER PUBLICATIONS

Edwards, Michael L., et al., "Stereospecific synthesis of secondary amines by the Mitsunobu reaction", "Tetrahedron Lett.", pp. 3417-3420, vol. 31, No. 24.

Fukuyama, Tohru, et al., "2- and 4-Nitrobenzenesulfonamides: Exceptionally versatile means for preparation of secondary amines and protection . . . ", "Tetrahedrom Lett.", Sep. 4, 1995, pp. 6373-6374, vol. 36, No. 36.

Fukuyama, Tohru, et al., "2,4-Dinitrobenzenesulfonamides: A simple and practical method for the preparation of a variety of secondary amines . . . ", "Tetrahedron Lett.", Aug. 18, 1997, pp. 5831-5834, vol. 38, No. 33.

Thomas, S.M., et al., "In-process test for synthesis of Dorzolamide Hydrochloride", "At-Process", 1997, pp. 432-439, vol. 2, No. 5-6.

*Primary Examiner*—Taofiq A Solola
(74) *Attorney, Agent, or Firm*—Steven J. Hultquist; Intellectual Property/Technology Law

(57) ABSTRACT

The invention is aimed at a compound of formula (I) wherein n is 0, 1 or 2, $R_1$ is a linear or branched alkyl group, $R_2$ is selected from a substituted or non substituted alkyl group, substituted or non substituted aryl group, substituted or non substituted aralkyl group, substituted or non substituted heterocyclyl group, or a substituted or non substituted heterocyclylalkyl group. Another object of the invention is a process for obtaining these compounds from the corresponding compound with a hydroxy group in position 4 by means of reacting with a sulfonamide in the presence of a phosphine and a dialkyl azadicarboxylate. The deprotection of the compound of formula (I) gives rise to the corresponding amine. The intermediate and the processes described are very useful in the synthesis of pharmaceutical products.

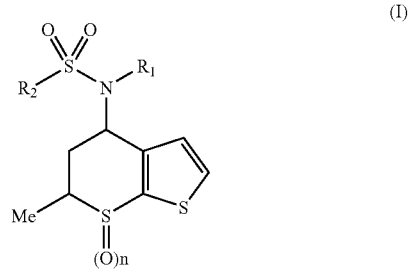

(I)

17 Claims, No Drawings

METHOD OF OBTAINING DERIVATIVES OF 4-(N-ALKYLAMINO)-5,6-DIHYDRO-4H-THIENO-[2,3-B]-THIOPYRAN

CROSS-REFERENCE TO RELATED APPLICATIONS

This application is filed under the provisions of 35 U.S.C. §371 and claims the priority of International Patent Application No. PCT/ES2005/000594 filed 4 Nov. 2005, which in turn claims priority of Spanish Patent Application No. P200402668 filed 5 Nov. 2004. The disclosures of said International Patent Application and Spanish Patent Application are incorporated herein by reference, in their respective entireties, for all purposes.

FIELD OF THE INVENTION

The invention relates to certain compounds useful as intermediates in the enantioselective synthesis of drugs, such as dorzolamide for example, as well as processes for obtaining them. It also relates to dorzolamide synthesis processes passing through these intermediates.

BACKGROUND OF THE INVENTION

Carbonic anhydrase inhibitors are used in the treatment of ocular hypertension (cause of the onset of glaucoma). European patent EP 296 879 B1 describes that, among other compounds, 4-(N-alkylamino)-5,6-dihydro-4H-thieno-[2,3-b]-thiopyran-2-sulfonamide-7,7-dioxides of general formula (VII)

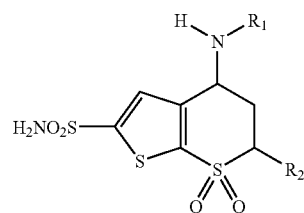

wherein $R_1$ is an alkyl and $R_2$ is a hydrogen atom or an alkyl, have carbonic anhydrase inhibitory activity when topically administered.

Among such compounds, the compound (4S,6S)-4-(N-ethylamino)-5,6-dihydro-6-methyl-4H-thieno-[2,3-b]-thiopyran-2-sulfonamide-7,7-dioxide, also known as dorzolamide, of formula:

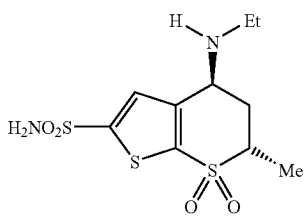

stands out.

Patent documents and applications EP 296 879 B1, U.S. Pat. No. 5,157,129, EP 617 037 and WO 02/20529 describe several synthetic routes for obtaining dorzolamide and analogues.

Documents U.S. Pat. No. 5,157,129 and WO 02/20529 describe enantioselective routes in which the sulfonamide group in position 2 is introduced in the final steps of the synthesis without affecting the stereochemistry of the intermediates. One of the key intermediates in both cases is the compounds with an amino group in position 4, of formula (II):

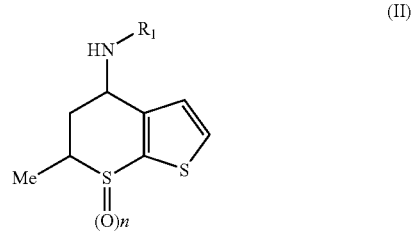

and its diastereoisomers.

To obtain it, U.S. Pat. No. 5,157,129 starts from a hydroxyl group in position 4, which is subjected to a tosylation reaction and subsequent nucleophilic substitution with an alkylamine:

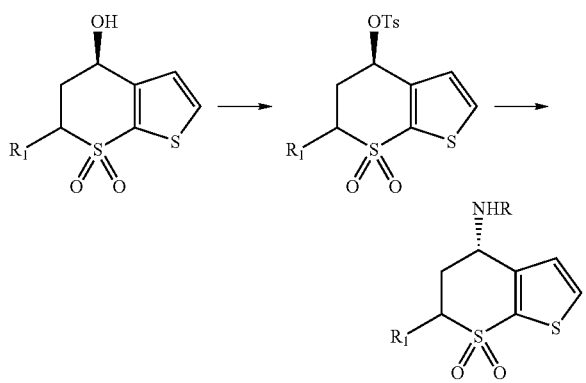

However, the introduction of the tosyl group is hindered due to the lack of reactivity of the hydroxyl group. Furthermore, once the compound is tosylated, as this is in a benzyl position, it is unstable and therefore susceptible to producing lateral reactions, such as the elimination, substitution with a chlorine group in the reaction conditions (if tosyl chloride is used) and if a compound is involved which has a sulfone group in position 6, even the substitution thereof with an oxygen for the sulfonyl group can occur.

There are few methods for converting a benzyl alcohol into the corresponding alkylamine in a completely diastereoselective manner. For example, U.S. Pat. No. 5,391,772 describes the introduction of an azide group on similar structures, also starting from a hydroxyl group in position 4, by means of the use of a phosphoryl azide group which results in inverting the configuration. In this case, however, prior synthesis of the phosphoryl azide is required, and the use of azides entails a certain hazard at the industrial level due to their toxicity and because they are potentially explosive.

Therefore, according to the state of the art, obtaining the alkylamines of formula (II) has several drawbacks because it involves at least 3-4 synthesis steps, some of which are hazardous. All this may further affect the diastereoselectivity in the subsequent amination, as well as the occurrence of byproducts.

SUMMARY OF THE INVENTION

This invention is aimed at stable intermediates and reactions for diastereoselectively preparing the aforementioned 4-(N-alkylamino)-5,6-dihydro-4H-thieno-[2,3-b]-thiopyrans solving the aforementioned drawbacks.

So in an aspect the invention is aimed at a compound of formula (I):

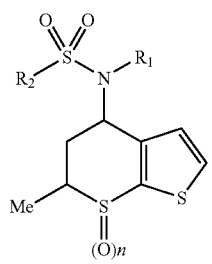
(I)

wherein:
n is 0, 1 or 2,
$R_1$ is a linear or branched alkyl group,
$R_2$ is selected from a substituted or non substituted alkyl group, substituted or non substituted aryl group, substituted or non substituted aralkyl group, substituted or non substituted heterocyclyl group, substituted or non substituted heterocyclylalkyl group,
their stereoisomers and/or mixtures thereof.

In another aspect the invention is aimed at a process for obtaining these compounds of formula (I) comprising the reaction, resulting in inverting the configuration of the carbon atom in position 4, of a compound of formula (III)

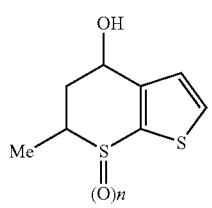
(III)

wherein n is 0, 1 or 2,
with a compound of formula (IV)

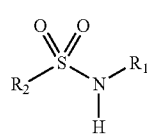
(IV)

wherein $R_1$ and $R_2$ are those previously defined,
in the presence of a phosphine and a dialkyl azadicarboxylate.

The invention is also aimed at a process for obtaining a compound of formula (II)

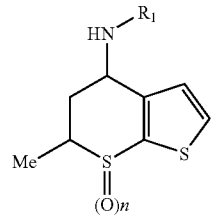
(II)

its stereoisomers or mixtures thereof, wherein n and $R_1$ are those previously defined, comprising deprotecting the amino group of a compound of formula (I) as it was previously defined. One variant of the process is aimed at obtaining alkylamines with a trans stereochemistry.

Finally in another aspect, the invention is also aimed at a process for the synthesis of (4S,6S)-4-(N-ethylamino)-5,6-dihydro-6-methyl-4H-thieno-[2,3-b]-thiopyran-2-sulfonamide-7,7-dioxide (Dorzolamide) comprising at least one of the two previously defined processes.

DETAILED DESCRIPTION OF THE INVENTION

The inventors have found a new synthetic route for diastereoselectively preparing 4-(N-alkylamino)-5,6-dihydro-4H-thieno-[2,3-b]-thiopyrans of general formula (I), useful for forming drugs for controlling ocular hypertension, such as dorzolamide for example. Starting from a hydroxyl group with a defined configuration (cis or trans, preferably cis) in position 4, the corresponding alkylamines with the opposite configuration (trans or cis, preferably trans) are obtained by means of a transformation of the following type:

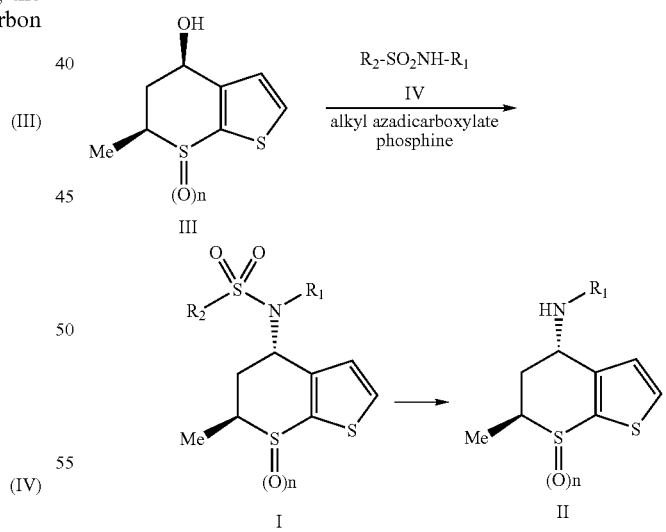

Surprisingly, the sulfonamide intermediates of general formula (I) are stable and solid that do not give rise to decomposition products. Furthermore the first reaction is completely diastereoselective with inversion of the configuration. An additional advantage is that the reaction conditions are mild and the reagents are not at all hazardous. The two-step synthesis reaction has very high yields and the obtained products are easy to purify.

Although Mitsunobu conditions have been used to convert alcohol to amines beforehand, in the case of the structures at hand the formation of elimination byproducts and the loss of stereochemical control on the carbon involved would be expected, as mentioned in U.S. Pat. No. 5,391,772 (col. 2, 1.44-col. 3, 1.10), resulting in mixtures requiring complicated purifications and therefore will little industrial application. Despite this fact, it has surprisingly been found that the amination reaction using nitrobenzenesulfonylamines occurs quickly and cleanly with the inversion of the configuration and with high yields giving rise to a stable compound which can be easily isolated, having the N directly protected by means of a group that can subsequently be easily eliminated.

Therefore an object of the invention is the compounds of formula (I):

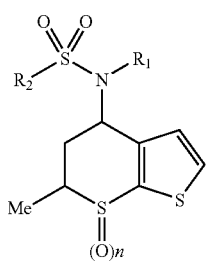

(I)

wherein n is 0, 1 or 2, $R_1$ is a linear or branched alkyl group, $R_2$ is selected from a substituted or non substituted alkyl group, substituted or non substituted aryl group, substituted or non substituted aralkyl group, substituted or non substituted heterocyclyl group, substituted or non substituted heterocyclylalkyl group, their stereoisomers and/or mixtures thereof.

In a variant of the invention the compound has n=0 or 2, n is preferably 2. In this case the intermediate is especially useful for preparing dorzolamide.

In another variant the group $R_1$ is an alkyl group with 1-4 carbon atoms, preferably ethyl.

In another variant of the invention, $R_2$ is a substituted or non substituted aryl group. Preferably $R_2$ is a benzene group such as 2-nitrobenzene or 4-nitrobenzene.

The compounds of the invention are especially useful when they have the trans configuration, including the corresponding enantiomers or mixtures thereof.

The following compounds are particularly preferred among the compounds of the invention:

4-[N-ethyl-N-(2-nitrobenzenesulfonyl)amino]-5,6-dihydro-6-methyl-4-H-thieno-[2,3-b]-thiopyran-7,7-dioxide, 4-[N-ethyl-N-(4-nitrobenzenesulfonyl)amino]-5,6-dihydro-6-methyl-4-H-thieno-[2,3-b]-thiopyran-7,7-dioxide, 4-[N-ethyl-N-(2-nitrobenzenesulfonyl)amino]-5,6-dihydro-6-methyl-4-H-thieno-[2,3-b]-thiopyran, their stereoisomers or mixtures thereof.

As previously mentioned, the trans stereoisomers of these compounds are preferred, i.e.:

trans-4-[N-ethyl-N-(2-nitrobenzenesulfonyl)amino]-5,6-dihydro-6-methyl-4-H-thieno-[2,3-b]-thiopyran-7,7-dioxide, trans-4-[N-ethyl-N-(4-nitrobenzenesulfonyl)amino]-5,6-dihydro-6-methyl-4-H-thieno-[2,3-b]-thiopyran-7,7-dioxide, trans-4-[N-ethyl-N-(2-nitrobenzenesulfonyl)amino]-5,6-dihydro-6-methyl-4-H-thieno-[2,3-b]-thiopyran, as well as their enantiomers or mixtures thereof.

A compound that is particularly preferred due to its direct usefulness for the synthesis of dorzolamide is:

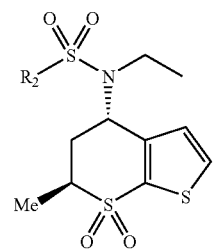

wherein $R_2$ has the previously mentioned meaning.

In this description, the following terms have the indicated meaning:

"Alkyl" refers to a saturated, linear or branched, hydrocarbonated chain radical that can have between 1 and 12 carbon atoms and is joined to the rest of the molecule by means of a single bond, for example, methyl, ethyl, n-propyl, i-propyl, n-butyl, t-butyl, n-pentyl, etc. If they are substituted, they can be substituted by one or more substituents such as aryl, halogen, hydroxyl, alkoxyl, carboxyl, cyano, carbonyl, acyl, alkoxycarbonyl, amino, nitro, mercapto, alkylthio, etc. If it is substituted by aryl, a radical "aralkyl", such as benzyl and phenethyl, is obtained. If it is substituted by heterocyclyl, a radical "heterocyclylalkyl" is obtained.

"Aryl" refers to single-ring and multi-ring radicals, both separated and condensed. Typical aryl groups contain from 1 to 3 separated or condensed rings and from 6 to about 18 ring carbon atoms, such as a radical phenyl, naphthyl, diphenyl, indenyl, phenanthryl or anthracyl, among others. If it is substituted, it can have one or more substituents, such as hydroxyl, mercapto, halogen, alkyl, phenyl, alkoxyl, haloalkyl, nitro, cyano, dialkylamino, aminoalkyl, acyl, alkoxycarbonyl, etc.

"Heterocyclyl" refers to a stable radical having a 3 to 15 member ring consisting of carbon atoms and from one to five heteroatoms selected from the group consisting of nitrogen, oxygen and sulfur, preferably a 4 to 8 member ring with one or more heteroatoms and, more preferably, a 5 or 6 member ring with one or more or heteroatoms. It may or may not be aromatic.

As previously mentioned, another object of the invention is a process for preparing the compounds of formula (I), comprising the reaction, resulting in inverting the configuration in the carbon atom in position 4, of a compound of formula (III)

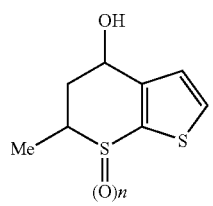

(III)

wherein n is 0, 1 or 2, with compound of formula (IV)

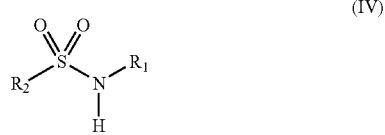

wherein $R_1$ and $R_2$ are those previously defined, in the presence of a phosphine and a dialkyl azadicarboxylate.

The carbinol of formula (III) is known and can be obtained, for example, according to the methodologies described in U.S. Pat. No. 5,157,129 and U.S. Pat. No. 5,760,249.

In a variant of the process of the invention, the phosphine is triphenylphosphine ($PPh_3$). In another variant, dialkyl azadicarboxylate is diisopropyl azadicarboxylate (DIAD) or diethyl azadicarboxylate (DEAD), although DIAD, which is more stable, is preferred.

Regarding the sulfonamide (IV) used, it can be easily obtained by reacting a sulfonyl chloride with the corresponding alkylamine. For example, N-ethyl-2-nitrobenzenesulfonamide is preferably obtained by reacting 2-nitrobenzenesulfonyl chloride with aqueous ethylamine at 0-5° C.

The reaction of 4-hydroxy-5,6-dihydro-4H-thieno-[2,3-b]-thiopyran (III) with sulfonamide (IV) is preferably carried out under nitrogen atmosphere in an aprotic solvent such as acetonitrile, methylene chloride, tetrahydrofuran, toluene, etc. The preferred solvent is toluene, given that some compounds of general formula (I) can precipitate in the reaction medium and can be isolated by simple filtration, preventing extractions or other more complicated separations.

In the described reaction, it is preferably that the reaction temperature be about −35° C. to 20° C. A preferred range is from −30° C. to 0° C.

Once the reagents are added, the reaction is maintained under stirring until the transformation has concluded. If a precipitate forms it can be filtered, the solid washed for example with cold toluene, acetonitrile or methylene chloride and dried.

The process of the invention described above is characterized by being completely diastereoselective, such that if the center 4 has configuration S in compound (III), a compound (I) with configuration R is obtained in position 4. And if cis-(III) is used as a starting material, trans-(I) is obtained. This is very important for obtaining pure pharmaceutical products by preventing mixtures of diastereómers requiring additional separation steps and reducing the process yield.

An additional object of the invention is also the process of deprotecting the compounds of formula (I), i.e. a process for obtaining a compound of formula (II)

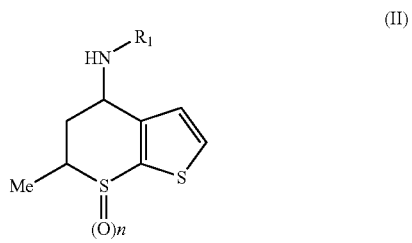

its stereoisomers or mixtures thereof, wherein n and $R_1$ are those previously defined, comprising deprotecting the amino group of a compound of formula (I) as previously defined.

This reaction is conditioned by the $R_2$ residue. The suitable selection of this substituent allows the deprotection reaction to occur easily in mild conditions known in organic synthesis.

When $R_2$ is, for example, 2-nitrophenyl or 4-nitrophenyl, deprotection is carried out by reaction with potassium phenylsulfide. In a typical process a solution of benzenethiol in acetonitrile is prepared and treated with an aqueous solution of potassium hydroxide at 0° C. to 10° C. The compound of formula (I) is loaded in the resulting mixture and heated at 40-50° C., until the transformation has concluded. During the transformation the reaction mixture goes from being a suspension to a solution. Once the transformation has concluded the mixture is treated with water, the volatiles are distilled and then the compound of formula (II) is extracted with an organic solvent, preferably ethyl acetate. The compound of formula (II) is isolated in said extraction.

Alternatively, the compound of formula (II) can be isolated, if desired, as an organic or inorganic acid salt by means of adding the corresponding organic or inorganic acid in the suitable solvent.

As can be seen, the intermediate (I) and the processes of the invention previously described are particularly useful in the synthesis of dorzolamide. Therefore, an additional object of the invention is the use of a compound of formula (I) in a dorzolamide synthesis process and in a dorzolamide synthesis process comprising a reaction step for reacting a carbinol (III) and a sulfonamide (IV) as previously described, or a deprotection step as previously described. In a preferred variant the process comprises both steps.

The invention is additionally illustrated by means of the following examples which cannot be interpreted as being limiting on the scope of the claims.

EXAMPLES

Example 1

N-ethyl-4-nitrobenzenesulfonamide

70% ethylamine in water (12.7 mL) and methanol (50 mL) are mixed. It is cooled to 0-5° C. 4-nitrobenzenesulfonyl chloride (10 g) is added portion-wise maintaining the temperature under 5° C. It is stirred for 15 minutes, maintaining the temperature, until the transformation is complete. Water (100 mL) is added. It is stirred for 30 minutes maintaining the temperature under 5° C. The reaction mixture is filtered, the isolated solid is washed with water and dried, obtaining 8.99 g of N-ethyl-4-nitrobenzene-sulfonamide.

Example 2 trans-4-[N-ethyl-N-(4-nitrobenzenesulfonyl)amino]-5,6-dihydro-6-methyl-4-H-thieno-[2,3-b]-thiopyran-7,7-dioxide Methylene chloride (60 mL), cis-4-hydroxy-5,6-dihydro-6-methyl-4-H-thieno-[2,3-b]-thiopyran-7,7-dioxide (5 g), N-ethyl-4-nitrobenzene-sulfonamide (6.86 g) and triphenylphosphine (8.42 g) are mixed under nitrogen atmosphere. The mixture is cooled to under −20° C. and diisopropyl azadicarboxylate (5.9 mL) is added, maintaining the temperature under −20° C. The temperature is allowed to rise to 20-25° C. The obtained mixture is treated with 5% NaOH (125 mL) and the resulting organic phase is vacuum distilled to dryness. The residue is chromatographed in a column (ethyl acetate/heptane, 2/1), obtaining 4.97 g of trans-4-[N-ethyl-N-(4-nitrobenzenesulfonyl)amino]-5,6-dihydro-6-methyl-4-H-thieno-[2,3-b]-thiopyran-7,7-dioxide.

$^1$H-NMR (DMSO-$d_6$, 400 MHz): δ (ppm)=0.96 (t, 3H); 1.30 (d, 3H); 2.24 (dt, 1H); 2.58 (ddd, 1H); 3.16 (m, 2H); 3.70 (m, 1H); 5.26 (dd, 1H); 6.60 (d, 1H); 7.93 (d, 1H); 8.2 (d, 2H); 8.40 (d, 2H).

$^{13}$C-NMR (DMSO-$d_6$, 100 MHz): δ (ppm)=12 ($CH_3$); 16 ($CH_3$); 34 ($CH_2$); 41 ($CH_2$); 52 (CH); 56 (CH); 126 (CH); 128 (CH); 129 (CH); 133 (CH); 136 (C); 143 (C); 146 (C); 151 (C).

Example 3

Trans-4-(N-ethylamino)-5,6-dihydro-6-methyl-4-H-thieno-[2,3-b]-thiopyran-7,7-dioxide hydrochloride (Starting from trans-4-[N-ethyl-N-(4-nitrobenzenesulfonyl)amino]-5,6-dihydro-6-methyl-4-H-thieno-[2,3-b]-thiopyran-7,7-dioxide)

Benzenethiol (2.8 mL) is dissolved in acetonitrile (14.5 mL) and cooled at 0-5° C. A solution of potassium hydroxide (1.53 g) in water (3.6 mL) is added maintaining the temperature. Trans-4-[N-ethyl-N-(4-nitrobenzenesulfonyl)amino]-5,6-dihydro-6-methyl-4-H-thieno-[2,3-b]-thiopyran-7,7-dioxide (4.69 g) is added. The resulting suspension is heated at 50° C. and the temperature is maintained until completing the transformation. It is cooled at 20-25° C. and water (36 mL) is added. The mixture is vacuum distilled until the acetonitrile has been removed. It is extracted with ethyl acetate (72 mL). The organic phase is vacuum distilled to dryness. The residue is dissolved in ethyl acetate (72 mL) and 35% hydrochloric acid (1 mL) is added. The resulting suspension is filtered. The isolated solid is washed with ethyl acetate and dried, obtaining 2.56 g of trans-4-(N-ethylamino)-5,6-dihydro-6-methyl-4-H-thieno-[2,3-b]-thiopyran-7,7-dioxide hydrochloride.

Example 4

N-ethyl-2-nitrobenzenesulfonamide 2-nitrobenzenesulfonyl chloride (10 g) is added portionwise to 70% ethylamine in water at 0-5° C., maintaining the temperature. It is stirred for 15 minutes until completing the transformation. Water (80 mL) is added, maintaining the temperature. It is stirred for 30 minutes. It is filtered, washed and dried, obtaining 8.97 g of N-ethyl-2-nitrobenzenesulfonamide.

$^1$H-NMR (CDCl$_3$, 400 MHz): δ (ppm)=1.15 (t, 3H); 3.15 (q, 2H); 5.25 (t, 1H); 7.7 (m, 2H); 7.8 (m, 1H); 8.10 (m, 1H).

$^1$C-NMR (CDCl$_3$, 100 MHz): ethylamine (ppm)=15 ($CH_3$); 39 ($CH_2$); 125.2 (CH); 131 (CH); 132.8 (CH); 133.4 (C); 133.8 (CH); 148 (C)

Example 5

Trans-4-[N-ethyl-N-(2-nitrobenzenesulfonyl)amino]-5,6-dihydro-6-methyl-4-H-thieno-[2,3-b]-thiopyran Methylene chloride (130.5 mL), cis-4-hydroxy-5,6-dihydro-6-methyl-4-H-thieno-[2,3-b]-thiopyran (10.44 g), N-ethyl-2-nitrobenzene-sulfonamide (16.78 g) and triphenyl-phosphine (20.61 g) are mixed under nitrogen atmosphere. The mixture is cooled at 0-5° C. and diisopropyl azadicarboxylate (16.6 mL) is added, maintaining the temperature. The temperature is allowed to rise to 20-25° C. and is maintained until completing the transformation (2 hours). The resulting mixture is treated with 5% NaOH (100 mL). The resulting organic phase is vacuum distilled to dryness and the residue is chromatographed, obtaining 9.8 g of trans-4-[N-ethyl-N-(2-nitrobenzenesulfonyl)amino]-5,6-dihydro-6-methyl-4-H-thieno-[2,3-b]-thiopyran.

$^1$H-NMR (CDCl$_3$, 400 MHz): δ (ppm)=1.05 (t, 3H); 1.45 (d, 3H); 2.17 (m, 1H); 2.35 (m, 1H); 3.16 (m, 1H); 3.39 (m, 1H); 3.48 (m, 1H); 5.2 (dd, 1H); 6.71 (d, 1H); 6.95 (d, 1H); 7.7 (m, 3H); 8.1 (m, 1H)

$^{13}$C-NMR (CDCl$_3$, 100 MHz): δ (ppm)=17 ($CH_3$); 21 ($CH_3$); 36 (CH); 37 ($CH_2$); 41 ($CH_2$); 52 (CH); 122 (CH); 124 (CH) 128 (CH); 129 (C); 131 (CH); 132 (CH); 133 (C); 134 (CH); 134.5 (C); 148 (C)

Example 6

Trans-4-(N-ethylamino)-5,6-dihydro-6-methyl-4-H-thieno-[2,3-b]-thiopyran

Benzenethiol (3.2 mL) is dissolved in acetonitrile (15 mL). It is cooled under 5° C. and a mixture of potassium hydroxide (1.73 g) in water (4.2 mL) is added, maintaining the temperature under 10° C. The temperature is allowed to rise to 20-25° C. and a solution of trans-4-[N-ethyl-N-(2-nitrobenzenesulfonyl)amino]-5,6-dihydro-6-methyl-4-H-thieno-[2,3-b]-thiopyran (4.9 g) in acetonitrile (10 mL) is added. The resulting mixture is heated at 50° C. and is maintained until completing the transformation. Water (80 mL) is added and it is vacuum distilled until the volatiles are removed. It is extracted with ethyl acetate (80 mL). The resulting organic phase is vacuum distilled to dryness and the obtained residue is chromatographed in a column (methylene chloride/methanol 94/6), obtaining 1.9 g of trans-4-(N-ethylamino)-5,6-dihydro-6-methyl-4-H-thieno-[2,3-b]-thiopyran.

$^1$H-NMR (CDCl$_3$, 400 MHz): δ (ppm)=1.10 (t, 3H); 1.25 (broad s, 1H); 1.38 (d, 3H); 1.71 (m, 1H); 2.22 (m, 1H) 2.72 (q, 2H); 3.58 (m, 1H); 3.82 (t, 1H); 6.85 (d, 1H) 6.98 (d, 1H).

$^{13}$C-NMR (CDCl$_3$, 100 MHz): δ (ppm)=16 ($CH_3$); 21 ($CH_3$); 33 (CH); 38 ($CH_2$); 42 ($CH_2$); 52 (CH); 121 (CH); 128 (CH) 131 (C); 134 (C).

Example 7

Trans-4-[N-ethyl-N-(2-nitrobenzenesulfonyl)amino]-5,6-dihydro-6-methyl-4-H-thieno-[2,3-b]-thiopyran-7,7-dioxide Toluene (100 mL); triphenylphosphine (6.8 g); cis-4-hydroxy-5,6-dihydro-6-methyl-4-H-thieno-[2,3-b]-thiopyran-7,7-dioxide (5 g) and N-ethyl-2-nitrobenzenesulfonamide (5.54 g) are mixed under nitrogen atmosphere. The mixture is cooled at −30° C. and diisopropyl azadicarboxylate (4.8 mL) is added. It is stirred until completing the transformation. It is filtered, washed and dried. The isolated raw product is column-purified to give 8.07 g of trans-4-[N-ethyl-N-(2-nitrobenzenesulfonyl)amino]-5,6-dihydro-6-methyl-4-H-thieno-[2,3-b]-thiopyran-7,7-dioxide.

$^1$H-NMR (CDCl$_3$, 400 MHz): δ (ppm)=1.0 (t, 3H); 1.55 (d, 3H); 2.55 (dt, 1H); 2.95 (ddd, 1H); 3.2 (m, 1H); 3.4 (m, 1H); 3.5 (m, 1H); 5.4 (dd, 1H); 7.0 (d, 1H); 7.55 (d, 1H); 7.75 (m, 3H); 8.15 (m, 1H).

$^{13}$C-NMR (CDCl$_3$, 100 MHz): δ (ppm)=12.5 ($CH_3$); 16.0 ($CH_3$); 33.0 ($CH_2$); 41 ($CH_2$); 51.5 (CH); 56.5 (CH); 124.5 (CH); 127.5 (CH); 130.5 (CH); 131.0 (CH); 132.5 (CH); 133.9 (C); 134 (CH); 135.3 (C); 142.0 (C); 147.5 (C).

Example 8

Trans-4-[N-ethyl-N-(2-nitrobenzenesulfonyl)amino]-5,6-dihydro-6-methyl-4-H-thieno-[2,3-b]-thiopyran-7,7-dioxide (Using tributylphosphine)

Toluene (100 mL); cis-4-hydroxy-5,6-dihydro-6-methyl-4-H-thieno-[2,3-b]-thiopyran-7,7-dioxide (5 g), tributylphosphine (6.6 mL) and N-ethyl-2-nitrobenzenesulfonamide (6.17 g) are mixed under nitrogen atmosphere. It is cooled at −20/−30° C. Diisopropyl azadicarboxylate (4.8 mL) is added, maintaining the temperature. It is maintained under stirring, maintaining the temperature, for 4 hours. Tributylphosphine (1.5 mL) and diisopropyl azadicarboxylate (1.5 mL) are added. It is left to reach 20-25° C. and maintained for 30 minutes. It is cooled at 0-5° C.; it is filtered, washed with cold toluene and dried. After purifying by resuspension in methanol, 2.01 g of trans-4-[N-ethyl-N-(2-nitrobenzenesulfonyl)amino]-5,6-dihydro-6-methyl-4-H-thieno-[2,3-b]-thiopyran-7,7-dioxide are obtained.

Example 9

Trans-4-(N-ethylamino)-5,6-dihydro-6-methyl-4-H-thieno-[2,3-b]-thiopyran-7,7-dioxide hydrochloride (Starting from trans-4-[N-ethyl-N-(2-nitrobenzenesulfonyl)amino]-5,6-dihydro-6-methyl-4-H-thieno-[2,3-b]-thiopyran-7,7-dioxide)

Benzenethiol (31.7 mL) is dissolved in acetonitrile (164.6 mL) and cooled at 0-5° C. A solution of potassium hydroxide (17.33 g) in water (34.7 mL) is added, maintaining the temperature. Trans-4-[N-ethyl-N-(2-nitrobenzenesulfonyl)amino]-5,6-dihydro-6-methyl-4-H-thieno-[2,3-b]-thiopyran-7,7-dioxide (53.11 g) is added and is heated to 50° C. until completing the transformation. It is cooled at 20-25° C. and water (410 mL) is added. The mixture is vacuum distilled until the volatiles have been removed. It is extracted with ethyl acetate (410 mL and 2×210 mL). The organic phases are pooled and treated with 35% hydrochloric acid (12 mL). It is vacuum distilled until the volume is reduced to half. It is filtered, washed with ethyl acetate and dried. 32.45 g of trans-4-(N-ethylamino)-5,6-dihydro-6-methyl-4-H-thieno-[2,3-b]-thiopyran-7,7-dioxide hydrochloride are obtained.

The invention claimed is:

1. A compound of formula (I):

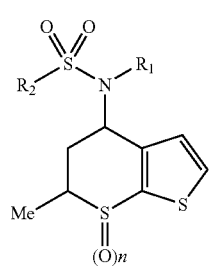

(I)

wherein:
n is 0, 1 or 2,
$R_1$ is a linear or branched alkyl group,
$R_2$ is 2-nitrobenzene or 4-nitrobenzene,
their stereoisomers and/or mixtures thereof.

2. A compound according to claim 1, wherein $R_1$ is an alkyl group with 1-4 carbon atoms, preferably ethyl.

3. A compound according to claim 1, wherein n is 0 or 2.

4. A compound according to claim 1, with the trans configuration including the corresponding enantiomers.

5. A compound according to claim 1, selected from:
4-[N-ethyl-N-(2-nitrobenzenesulfonyl)amino]-5,6-dihydro-6-methyl-4-H-thieno-[2,3-b]-thiopyran-7,7-dioxide,
4-[N-ethyl-N-(4-nitrobenzenesulfonyl)amino]-5,6-dihydro-6-methyl-4-H-thieno-[2,3-b]-thiopyran-7,7-dioxide,
4-[N-ethyl-N-(2-nitrobenzenesulfonyl)amino]-5,6-dihydro-6-methyl-4-H-thieno-[2,3-b]-thiopyran,
their stereoisomers or mixtures thereof.

6. A compound according to claim 5, selected from:
trans-4-[N-ethyl-N-(2-nitrobenzenesulfonyl)amino]-5,6-dihydro-6-methyl-4-H-thieno-[2,3-b]-thiopyran-7,7-dioxide,
trans-4-[N-ethyl-N-(4-nitrobenzenesulfonyl)amino]-5,6-dihydro-6-methyl-4-H-thieno-[2,3-b]-thiopyran-7,7-dioxide,
trans-4-[N-ethyl-N-(2-nitrobenzenesulfonyl)amino]-5,6-dihydro-6-methyl-4-H-thieno-[2,3-b]-thiopyran,
their enantiomers or mixtures thereof.

7. A process for obtaining a compound according to claim 1 comprising the reaction, with the resulting inversion of the configuration in the carbon atom in position 4, of a compound of formula (III)

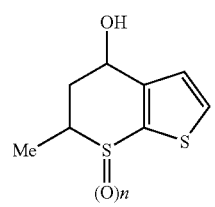

(III)

wherein n is 0, 1 or 2,
with a compound of formula (IV)

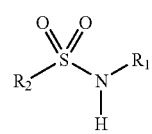

(IV)

wherein $R_1$ and $R_2$ are those previously defined,
in the presence of a phosphine and a dialkyl azadicarboxylate.

8. A process according to claim 7, wherein the phosphine is triphenylphosphine.

9. A process according to claim 7, wherein the dialkyl azadicarboxylate is diethyl or diisopropyl azadicarboxylate azadicarboxylate.

10. A process according to claim 7, characterized in that it is carried out in an aprotic solvent.

11. A process according to claim 7, wherein the compound (III) has the cis configuration.

12. A process for obtaining a compound of formula (II)

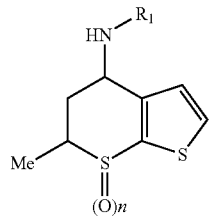

(II)

wherein:
n is 0, 1 or 2,
$R_1$ is a linear or branched alkyl group,
their stereoisomers or mixtures thereof,
comprising deprotecting the amino group of a compound according to claim 1.

13. A process according to claim 12, wherein $R_2$ is 2-nitrobenzene or 4-nitrobenzene and the deprotection is done in the presence of potassium phenylsulfide.

14. A process for the synthesis of (4S,6S)-4-(N-ethylamino)-5,6-dihydro-6-methy-4H-thieno-[2,3-b]-thiopyran-2-sulfonamide-7,7-dioxide (dorzolamide) comprising the process according to claim 7.

15. A process for the synthesis of (4S,6S)-4-(N-ethylamino)-5,6-dihydro-6-methyl-4H-thieno-[2,3-b]-thiopyran-2-sulfonamide-7,7-dioxide (Dorzolamide) comprising a process according to claim 7.

16. A process for obtaining a compound of formula (I)

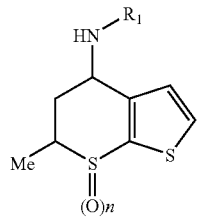

(II)

wherein n is 0, 1 or 2,
$R_1$ is a linear or branched alkyl group,
their stereoisomers or mixtures thereof,
comprising the reaction, with the resulting inversion of the configuration in the carbon atom in position 4, of a compound of formula (III)

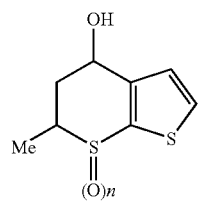

(III)

wherein n is 0, 1 or 2,
with a compound of formula (IV)

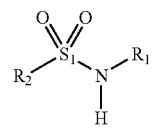

(IV)

wherein
$R_1$ is as previously defined, and
$R_2$ is 2
nitrobenzene or 4-nitrobenzene,
in the presence of a phosphine and a dialkyl azadicarboxylate, to yield a compound of formula (I)

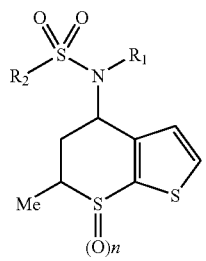

(I)

wherein n, $R_1$ and $R_2$ are as previously defined, and further deprotection of the amino group.

17. A process according to claim 10 wherein the aprotic solvent is toluene.

* * * * *